United States Patent [19]

Pate et al.

[11] Patent Number: 4,897,098
[45] Date of Patent: Jan. 30, 1990

[54] FRACTIONATION SYSTEM FOR STABILIZING NATURAL GASOLINE

[75] Inventors: Robin M. Pate, Houston; James O. Nye, Friendswood; David R. Keck, Seabrook, all of Tex.

[73] Assignee: Enterprise Products Company, Houston, Tex.

[21] Appl. No.: 196,764

[22] Filed: May 11, 1988

Related U.S. Application Data

[63] Continuation of Ser. No. 919,446, Oct. 16, 1986, abandoned.

[51] Int. Cl.⁴ .............................................. F25J 3/02
[52] U.S. Cl. .............................................. 62/31; 62/24; 62/28; 62/34
[58] Field of Search ..................... 62/9, 11, 23, 24, 27, 62/28, 31, 32, 34, 42

[56] References Cited

U.S. PATENT DOCUMENTS

| | | | |
|---|---|---|---|
| 2,916,888 | 12/1959 | Cobb, Jr. ................................. | 62/33 |
| 2,952,983 | 9/1960 | Gilmore .............................. | 62/27 X |
| 2,954,341 | 9/1960 | Stiles . | |
| 3,055,826 | 9/1967 | Arnett . | |
| 3,150,199 | 9/1964 | Greco et al. . | |
| 3,192,732 | 7/1965 | Cahn ...................................... | 62/17 |
| 3,324,010 | 6/1967 | Banes et al. . | |
| 3,405,530 | 10/1968 | Denahan et al. ....................... | 62/28 |
| 3,489,678 | 1/1970 | Moon et al. . | |
| 4,115,086 | 9/1978 | Jordon et al. ....................... | 62/39 X |
| 4,256,541 | 3/1981 | Muller et al. . | |
| 4,273,566 | 6/1981 | Schwarz .................................. | 62/27 |
| 4,336,046 | 6/1982 | Schasse et al. ........................... | 62/28 |
| 4,368,061 | 1/1983 | Mestrallet et al. ...................... | 62/28 |
| 4,372,822 | 2/1983 | Muller et al. . | |
| 4,460,396 | 7/1984 | Kaiser et al. ............................ | 62/28 |
| 4,496,386 | 1/1985 | Harryman .............................. | 62/24 |
| 4,555,311 | 11/1985 | Ward . | |
| 4,597,788 | 7/1986 | Apffel ................................ | 62/28 X |

Primary Examiner—Ronald C. Capossela
Attorney, Agent, or Firm—Kenneth H. Johnson

[57] ABSTRACT

Improved operation of an LPG fractionating facility having a deethanizer, depropanizer and debutanizer is obtained by operating the deethanizer at a lower pressure than conventional, (e.g., less than 500 psig), thereby reducing the temperature of the deethanizer bottoms such that the debutanizer operated at greater than conventional pressure (e.g., over 100 psig) produces a mixed butane overhead at a higher temperature than the deethanizer bottoms whereby the mixed butane overhead is condensed and cooled by indirect contact with the deethanizer bottoms thereby heating the bottoms and supplying a substantial portion of the energy required for the fractionation in the deethanizer. The energy reduction for the three column system through the improved heat recovery system is 10% to 50% depending upon the feed composition.

11 Claims, 1 Drawing Sheet

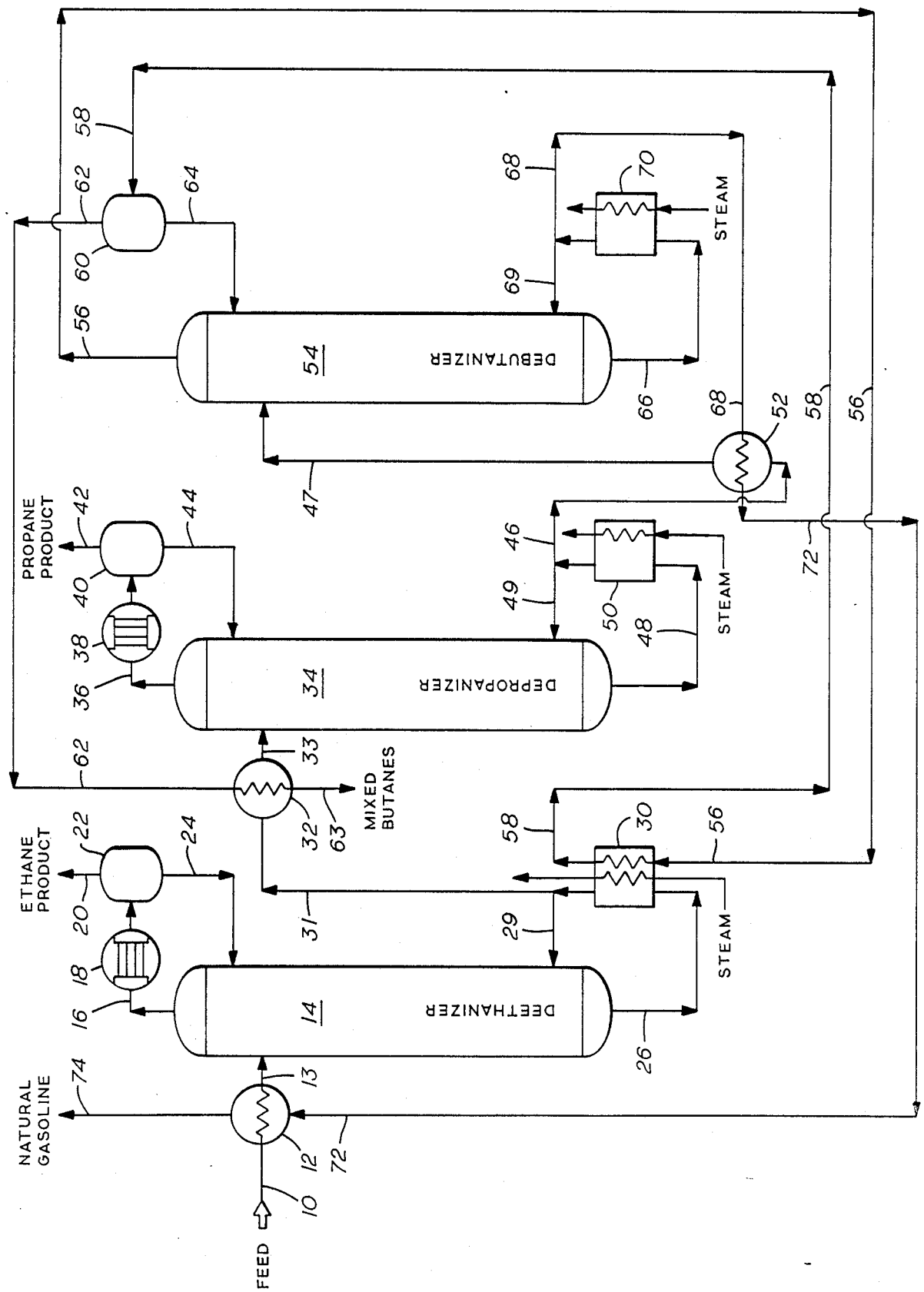

FRACTIONATION SYSTEM FOR STABILIZING NATURAL GASOLINE

This application is a continuation of application Ser. No. 919,446, filed Oct. 16, 1986, now abandoned.

BACKGROUND OF THE INVENTION

1. Field of the Invention

The present invention relates to a system and process for the separation of liquid hydrocarbon gases into components by fractionation. More particularly the invention relates to adapting and interrelating the fractionating units of an LPG (liquified petroleum gas) fractionating system to obtain at least a portion of the energy to operate the system from within the system itself.

2. Related Art

Natural gasoline is derived by condensation of vapors from gas wells of normally liquid hydrocarbons representing light gasoline fractions. Gas containing such vapors is referred to as "wet gas" or "rich gas" to distinguish it from "dry gas" or "lean gas", which is essentially free from them. Removal of gasoline vapors from natural gas used for heating purposes is required also because of potential fire hazard.

Hydrocarbons present in natural gas are of the saturated type, methane having the lowest boiling point and existing in the vapor form under most conditions. The greater the number of carbon atoms in the molecule, the higher the boiling point. These hydrocarbons include ethane ($C_2H_6$), propane ($C_3H_8$), butane ($C_4H_{10}$), pentane ($C_5H_{12}$) and the heavier ones in decreasingly smaller quantities.

Ethane is a gas similar to methane. Propane, which is also a gas under normal conditions, however, may be liquefied by applying considerable pressure. Butane liquifies with still greater ease because its boiling point under normal atmospheric pressure is still higher, close to the freezing point of water.

Liquid hydrocarbons present in natural gas and boiling within the gasoline range (butanes, pentanes and heavier) are referred to under the name of "natural gasoline." Motor fuel sold at the service stations is a blend of various petroleum products, including natural gasoline or its equivalents. The presence of dissolved gases is undesirable if natural gasoline is used for the preparation of the motor gasoline. Separation of these gases from the liquid hydrocarbon portion is, therefore, very important in commercial practice. This separation is accomplished by the "stabilization processes" and the resulting gasoline is referred to as "stabilized gasoline."

Stabilization of gasoline consists in separating gaseous and liquid hydrocarbons by what is known as fractional distillation. Fractional distillation is a process by which the vapors given off are passed through columns containing numbers of plates of special design. The plates have narrow passages for gases and vapors flowing upward. These vapor passages in the plates can be any one or mixtures of vapor dispersion devices such as bubble caps, sieve trays, valve trays, etc. The overflow pipes or liquid downcomers are reserved for liquid traveling downward and may be of various geometric configurations. At each plate the vapors condense and the resulting liquid partially revaporizes. The newly formed vapors ascend to the next higher plate of the fractionating column, while the condensed vapors and unevaporated fraction flows downward to the next plate below. After each revaporization the ascending vapors become progressively richer in the low-boiling materials. The process thus permits separation of liquid hydrocarbon mixtures into groups that boil within narrow temperature ranges or into individual hydrocarbons, if their boiling points differ considerably from the rest of the hydrocarbons in a mixture.

Stabilization of gasoline results in the reduction of its vapor pressure, i.e., the pressure that is registered when gasoline is confined in a closed vessel under prescribed conditions of testing. The desired vapor pressure is obtained by varying the content of lighter hydrocarbons, for example, propane and butane. In general, propane is an undesirable constituent of gasoline in the engine in any proportions. If gasoline contains an excess of butane, this excess may be separated and then added to another gasoline deficient in butane; conversely, if the gasoline is deficient in butanes, pure components from another source may be blended back into the gasoline. When propane is removed, the process is referred to as the "depropanizing process" and the fractionating column in which this is accomplished is known as a "depropanizer." When butane is removed, the process is referred to as the "debutanizing process," and the equipment is known as a "debutanizer." Similarly a "deethanizer" is employed for equipment for separating ethane and a "depentanizer" for equipment for separating pentane, a hydrocarbon boiling at a higher temperature than butane, from the heavier portion of the natural gasoline.

Fractionation of LPG, e.g., raw natural gasoline (U.S. Pat. No. 3,055,826, Arnett) and hydrocarbon conversion products (U.S. Pat. No. 2,954,341, Stiles), to recover the components such as methane, ethane, propane, butane and gasoline is conventional, although there may be variations in the sequence of component removal, conditions and configuration of equipment used in such fractionations and other similar fractionations. For example, U.S. Pat. No. 4,460,396, Kaiser, et al. discloses recovering ethylene from a $C_2$ stream using two columns with the overhead from the second column heat exchanged with the reboil of the first column; and U.S. Pat. No. 3,150,199, Greco, et al. discloses deethanizing and debutanizing followed by depropanizing hydrocarbon streams. Other fractionations have used an overhead from one column to heat the reboil of another column such as U.S. Pat. Nos. 2,916,888 (Cobb); 3,324,010 (Bauer, et al.); 4,256,541 (Muller, et al.); 4,372,822 (Muller, et al.); and 4,555,311 (Ward).

The same fractionation and heat utilization techniques also are employed in the separation of the various components of hydrocarbon mixtures from other sources. e.g., pyrolysis, cracking, hydroforming, isomerization, etc. These components can be saturated, unsaturated, aromatic or naphthenic. These components or cuts (mixtures of components) may, in addition to providing natural gasoline, provide raw materials for various petrochemicals, plastics, or synthetic rubber It is an advantage of the present invention that the deethanizer is operated in a manner to provide more efficient operation and greater capacity than previously. It is a further advantage that the debutanizer is operated in a manner to recover all of the heat from the overhead vapors normally wasted and utilize it to provide some of the heat required for separation of other components of the fractionation system. It is a feature of the present invention that the deethanizer is operated at temperatures and pressure sufficiently low so that the waste heat from the debutanizer overhead provides a substantial a portion of the energy for the operation of the deethanizer reboiler. These and other advantages and features will become apparent from the following description.

SUMMARY OF THE INVENTION

Briefly, the present invention is a system and process for fractionating liquid hydrocarbon gases comprising a deethanizer and a debutanizer wherein the deethanizer is operated under pressure conditions whereby the temperature of the bottoms in the deethanizer is below the temperature of the overhead of the debutanizer whereby the debutanizer overhead provides at least a portion, and preferably a substantial portion, of the energy for the operation of the deethanizer by vaporizing a portion of the deethanizer bottoms and returning that portion of the bottoms to the deethanizer.

In order to obtain this beneficial utilization of energy within the system, which would otherwise be waste heat, the deethanizer is operated at a lower pressure than is conventional. By reducing the pressure in the column, the temperature in the column for a given composition is also reduced. Simultaneously the debutanizer is operated at a substantially higher pressure than conventional whereby the temperature of the overhead mixed butane vapors is increased.

The waste heat is recovered by employing the overhead debutanizer vapor to provide reboil heat required by the deethanizer in a heat exchanger, thereby condensing the mixed butane vapor. LPG or similar feed to the system may comprise propane, ethane, butane and usually heavier petroleum components (e.g., natural gasoline).

For example, when the deethanizer is operated at a pressure of 370 psig (which is about 90 psig less than normal practice), and the debutanizer is operated at 270 psig (which is about 150 psig above normal pressure), the condensing temperature of the debutanizer overhead vapors will be about 225° F., substantially greater than the boiling temperature of the deethanizer bottoms, 198° F., permitting heat of condensation of the butane vapors to be indirectly transferred to the deethanizer bottoms, replacing an externally supplied heat source.

The maximum pressure for the deethanizer is 300 psig, and preferably more than 200 psig. In order to provide energy (heat) to provide reboil at this temperature the debutanizer is operated at least at 100 psig and preferably less than 400 psig.

In addition to the deethanizer and debutanizer a depropanizer may be included in a preferred system with the depropanizer also operated at lower than conventional pressure with waste heat from the debutanizer overhead product being used to preheat the depropanizer feed.

BRIEF DESCRIPTION OF THE DRAWING

The figure is a schematic representation of a preferred fractionation system for the separation of raw natural gasoline. The same system could be employed in the separation of a mixture of $C_2$, $C_3$, $C_4$ and $C_5+$ hydrocarbons from any source or process.

DETAILED DESCRIPTION OF THE INVENTION AND PREFERRED EMBODIMENT

The present invention is concerned with deethanizing, depropanizing and debutanizing hydrocarbon mixtures and recovering the various components.

The deethanizer separates the ethane from the propane and heavier components by fractional distillation. Vapor from the reboiler passes up the tower where it is mixed with liquid from the tower reflux passing down the tower across each tray. The vapor and liquid are mixed and then separated with the vapor rising to the tray above and the liquid falling to the tray below. Since ethane is relatively more volatile than propane and the other components, it tends to be more concentrated in the vapor phase, while the propane and heavier components remain in the liquid phase. By the time the vapor reaches the top of the tower it has concentrated to the point where it is high purity ethane product. Likewise, by the time the liquid reaches the bottom of the tower, most of the ethane has been removed, i.e., enough that the propane produced overhead in the depropanizer column will meet specification.

The ethane vapors from the top of the column are condensed by refrigeration. Some of the liquid is returned to the tower as reflux to provide the liquid for the vapor-liquid contacting that occurs on each tray. The balance goes to storage as high purity ethane product. At the bottom of the tower the liquid from the last tray enters the reboiler. Here it is heated and partially vaporized to provide the vapor that will travel up the tower. The unvaporized liquid is then fed to the depropanizer.

In the depropanizer, propane is separated from isobutane and heavier components by a process similar to that described for the deethanizer. The propane goes overhead as vapor and is condensed. The isobutane and heavier components go out the bottom. A portion of the condensed propane is then refluxed back to the tower and the remainder is yielded to storage. The unvaporized liquid (bottoms) is fed to the debutanizer.

In the debutanizer, the butanes are separated from feed in a similar manner to that described above. The butanes go on to another unit for further fractionation and the bottoms, containing pentanes and higher boiling components usually a gasoline, e.g., natural gasoline goes to treating and then to storage. Higher operating pressure of the debutanizer, while taking more energy, does not require more overall energy, since all of it is recovered in the deethanizer reboiler.

In the present invention the system and process relate to the fractionation of hydrocarbon streams containing ethane and heavier or higher boiling hydrocarbons, preferably alkanes characterized as liquid petroleum gas (LPG), e.g., raw natural gasoline and straight run gasoline derived from distillation, cracking higher molecular weight petroleum materials (crudes, tar sand oils, shale oils), "wet" natural gas and the like. Generally the streams treated will contain the lower alkanes, ethane, propane, butanes and the higher alkanes, pentanes ($C_5$), hexanes ($C_6$) through decane ($C_{10}$) or higher and also may contain aromatics. In addition to the alkanes, streams from cracking processes may also contain alkenes (unsaturated hydrocarbons) such as ethylene, propylene, butylene, etc. and small amounts of alkynes and other hydrocarbons. The pentane and heavier portion of the stream may have a boiling point of up to about 400° F. depending on the constituents in the feed mixture. The amounts of constituents may vary widely. Generally the streams which are contemplated obtain benefits in energy saving for the process may contain 15 to 40 wt.% ethane 20 to 50 wt.% propane and 20 to 50 wt.% mixed butane and 10 to 40 wt.% $C_5$ and higher hydrocarbons.

The figure shows in schematic form the usual basic components of a fractionating system, i.e., a deethanizer 14, a depropanizer 34 and a debutanizer 54. In this preferred embodiment, the feed 10 for example raw natural gasoline containing ethane, propane, mixed butanes, pentanes and higher alkanes enters deethanizer 14 through heat exchanger 12 where it is preheated by natural gasoline product (pentanes and higher) coming from the debutanizer 54 via line 72 and line 13. The feed enters the heat exchanger 12 and after indirect heat exchange with the natural gasoline product stream 72 it passes via line 13 to the deethanizer and the natural gasoline product is recovered from 74.

The deethanizer is a conventional fractionator equipped with trays and according to the present invention, operated on overhead pressure in line 16 of about 389 psig. At this pressure the temperature of the bottoms leaving via line 26 is about 181° F. The bottoms are directed via line 26 to reboiler 30 where this stream is heated and a portion vaporized and recycled to the deethanizer via 29 to provide the energy for the boil up in the column.

A substantial portion of the energy to heat the bottoms from the deethanizer column in the reboiler is provided by the mixed butane overhead from debutanizer 54 supplied through line 56 at a higher temperature than the temperature of the deethanizer bottoms. The mixed butanes are cooled and condensed by heat exchange with the cooler bottoms of the deethanizer, item 30, then returned via line 58 to the debutanizer section of the system to be described hereafter.

A high purity ethane overhead at line 16 which is cooled by refrigeration in condenser 18 and passed to accumulator 22 from whence a portion is recycled as reflux via line 24 and the remainder recovered as ethane product via 20.

The bottoms from the deethanizer ultimately pass to the depropanizer 34 via line 26 through heat exchanger 30 and line 31 through heat exchanger 32 and line 33. The heat exchanger 32 provides indirect contact between the feed to the depropanizer and the mixed butanes recovered from the debutanizer accumulator 60. The mixed butanes after having been condensed by heat exchange in reboiler 30 as described above are returned to the debutanizer accumulator 60 via line 58 where a portion of the mixed butanes are returned to the debutanizer 54 as via line 64 as reflux. The remaining recovered mixed butanes may preferably be used to preheat the feed to the depropanizer by directing a stream via line 62 to heat exchanger 32 before going to storage or other downstream processing units.

In the depropanizer butanes and heavier materials, i.e., $C_4+$, accumulate in the bottoms and are removed via 46 with a portion being recycled through reboiler 50 via lines 48 and 49. The energy to the reboiler in this section may be supplied by steam or other natural energy source. The balance of the bottoms which is now substantially free of $C_3$ and lighter hydrocarbons is the feed to the debutanizer 54. The depropanizer is also preferably operated at a lower pressure than is conventional for a fractionation plant and hence lower energy is required. The overhead which is substantially pure propane is recovered through line 36, condenser 38 and accumulator 40. Propane product is recovered via 42 and a portion is returned via 44 to the column as reflux.

The bottoms 46 recovered from the depropanizer provide the feed to the debutanizer, preferably after being preheated in heat exchanger 52 with the bottoms product 68 from the debutanizer (as described above, this same stream is used to preheat the feed 10 entering through exchanger 12). The energy for the debutanization which is supplied through the reboiler 70 may be provided by steam or other external energy source. The bottoms pass via 66 to the reboiler 70 where the stream is heated, a portion is vaporized and returned to the debutanizer via line 69 and the remainder passed via line 68 to heat exchanger 52 where it preheats the debutanizer feed. The preheated depropanized bottoms enters debutanizer 54 via 47. There the $C_4$'s, (isobutane and n-butanes), are recovered overhead via 56 and condensed in deethanizer reboiler 30 (as described). The condensed $C_4$'s are returned via line 58 to debutanizer accumulator 60, from whence a portion is recycled via 64 as reflux and the remainder is recovered from line 63 via 62 as described and used to preheat the feed to the depropanizer in heat exchanger 32. The mixed butane product which comprises n-butanes and isobutane is usually split to recover the two components. A highly efficient method for this split is disclosed in U.S. Pat. No. 4,336,046.

In the schematic for the present invention many conventional items of equipment such as valves, pumps, compressors, pressure reduction equipment and the like are not included, but are obvious expedients to those in the art. In order to further clarify the mode of operation of the present invention, the operating conditions for a typical operation using a raw natural gas liquids feed and described by the heat and material balance is set forth in the TABLE. The conditions in a stream, e.g., temperatures and pressures, will indicate equipment, if not specified, to obtain those conditions. The TABLE is based on 100,000 #/hr raw feed containing 23 wt.% ethane and the balance propane, mixed butanes and $C_5$ and higher hydrocarbons having boiling points above that of mixed butanes The Stream No. in the TABLE refers to the corresponding stream in the figure.

The sizing of equipment, column trays and types and the like are readily determinable by those in the art. It has been determined that energy saving for a fractionation plant operated in the manner of the preferred embodiment illustrated here compared to past operation of the plant is over 200 BTU's per gallon of feed, which is a savings of 4,000,000 BTU's per hour for the size plant illustrated. It was also found that the capacity of the plant was increased and the overall effect was to allow the facility, when operated according to the invention, to process 35% more feed without an increase in fuel consumption.

TABLE

| STREAM NO | STREAM DESCRIPN | TEMP °F | PRESS PSIG | FLOW LBS/HR | ENTHALPY MM BTU/HR | MOLE WT. | DENSITY LBS/CU FT |
|---|---|---|---|---|---|---|---|
| 10 | Feed | 102 | 475 | 100,000 | −12.123 | 45.71 | 30.64 |
| 13 | heated feed | 127.01 | 465 | 100,000 | −10.387 | 45.71 | 28.81 |

TABLE-continued

| STREAM NO | STREAM DESCRIPN | TEMP °F | PRESS PSIG | FLOW LBS/HR | ENTHALPY MM BTU/HR | MOLE WT. | DENSITY LBS/CU FT |
|---|---|---|---|---|---|---|---|
| 16 | deethanizer overhead | 39.74 | 370.0 | 72,432 | −2.202 | 30.10 | 3.44 |
| 24 | deethanizer reflux | 38.04 | 365.0 | 50,624 | −7.815 | 30.10 | 23.87 |
| 26 | deethanizer bottoms | 180.99 | 375 | 182,379 | −11.703 | 49.66 | 27.20 |
| 29 | deethanizer reboil | 198.09 | 375 | 104,247 | 4.297 | 47.15 | 4.04 |
| 31 | deethanizer bottoms | 167.69 | 220 | 78,192 | −3.797 | 53.44 | 6.84 |
| 33 | depropanizer feed | 168.69 | 210 | 78,192 | −2.802 | 56.43 | 5.09 |
| 36 | depropanizer overhead | 104.95 | 200 | 104,468 | 1.148 | 43.19 | 1.92 |
| 44 | depropanizer reflux | 96.25 | 195 | 72,148 | −9.142 | 43.19 | 25.45 |
| 46 | depropanizer bottoms | 228.26 | 335 | 45,870 | −1.855 | 64.17 | 29.99 |
| 48 | depropanizer bottoms | 219.19 | 204.5 | 102,128 | −4.746 | 62.46 | 29.78 |
| 49 | depropanizer reboil | 229.35 | 204.6 | 56,278 | 3.735 | 61.13 | 2.49 |
| 47 | debutanizer feed | 258.82 | 325 | 45,870 | −0.864 | 64.17 | 28.80 |
| 56 | debutanizer overhead | 227.57 | 275 | 99,256 | 5.966 | 58.16 | 3.48 |
| 64 | debutanizer reflux | 225.28 | 313 | 72,593 | −2.587 | 58.16 | 27.57 |
| 62 | debutanizer overhead | 225.28 | 272 | 27,455 | −0.989 | 58.16 | 27.57 |
| 63 | mixed butanes | 177.69 | 235 | 27,455 | −1.985 | 58.16 | 29.62 |
| 66 | debutanizer bottoms | 331.13 | 281 | 135,557 | 5.952 | 75.08 | 27.28 |
| 68 | debutanizer bottoms | 338.54 | 281 | 18,415 | 0.676 | 75.85 | 27.28 |
| 69 | debutanizer reboil | 338.54 | 281 | 117,142 | 13.843 | 74.47 | 4.09 |
| 72 | debutanizer bottoms | 265.88 | 256 | 18,415 | −0.391 | 75.85 | 31.83 |
| 74 | natural gasoline | 115.76 | 215 | 18,415 | −2.127 | 75.85 | 38.04 |

The invention claimed is:

1. A process for fractionating liquid hydrocarbons comprising:
  (a) fractionating a hydrocarbon stream comprising ethane and mixed butanes in a deethanizing fractionation zone operated at a pressure to produce a first temperature in the bottoms of said deethanizing zone;
  (b) separating said ethane as an overhead product and recovering the bottoms containing said mixed butanes from said deethanizing zone;
  (c) fractionating said bottoms containing mixed butanes in a debutanizing fractionation zone operated at a pressure to produce a mixed butane overhead at a second temperature sufficiently higher than said first temperature, whereby indirect contact between the mixed butane overhead and said bottoms of said deethanizing zone will cause heat to be transferred from said mixed butanes overhead to said bottoms; and
  (d) indirectly contacting said mixed butane overhead from said debutanizing zone with said bottoms from the deethanizing fractionation zone thereby substantially condensing said mixed butanes overhead.

2. The process according to claim 1 wherein said hydrocarbon stream additionally comprises propane.

3. The process according to claim 2 wherein said bottoms containing mixed butanes and propane from said deethanizing fractionation zone are fractionated in an intermediate fractionating zone prior to said debutanizing fractionation zone, recovering propane as an overhead product and an intermediate bottoms containing said mixed butanes and heavier hydrocarbons as the bottoms of said intermediate fractionation zone and fractionating said intermediate bottoms in said debutanizing fractionation zone.

4. The process according to claim 1 wherein said deethanizing fractionation zone is operated at a pressure of 500 psig or less.

5. The process according to claim 4 wherein said pressure in the deethanizing fractionation zone is more than 200 psig.

6. The process according to claim 4 wherein the debutanizing fractionation zone is operated at a pressure of at least 100 psig.

7. The process according to claim 6 wherein the pressure in the debutanizing fractionation zone is below 400 psig.

8. In a process for separating $C_4$ and lower molecular weight hydrocarbons from liquid petroleum gas (LPG) comprising ethane, propane and mixed butanes which comprises:
  (a) a first fractionation zone for separating and recovering ethane from said LPG as overhead and recovering as bottoms, low ethane LPG which comprises propane and mixed butanes;

(b) a second fractionation zone for separating recovering propane, as overhead, from said low ethane LPG bottoms of (a), and recovering, as bottoms therein, LPG substantially free of ethane and propane and comprising mixed butanes; and
(c) a third fractionation zone for separating and recovering mixed butanes, as overhead, from said bottoms of (b) and recovering, as bottoms therein, LPG substantially free of ethane, propane and having reduced mixed butanes; wherein the improvement comprises operating said first fractionating zone at a pressure of 500 psig or less whereby the bottoms of said first fractionating zone are at a first temperature and operating said third fractionation zone at a pressure of at least 100 psig whereby the overhead of said third fractionation zone is at a second temperature, said second temperature being higher than said first temperature and indirectly contacting said overhead from said third fractionation zone with the bottoms of said first fractionating zone to transfer heat from said overhead to said bottoms to thereby substantially condense said overhead and supply a substantial portion of the energy for the fractionation of the first fractionation zone.

9. The process according to claim 8 wherein the pressure in the third fractionation zone is in the range of 100 to 400 psig.

10. The process according to claim 8 wherein said LPG is raw natural gasoline.

11. The process according to claim 8 wherein said LPG is straight run gasoline.

* * * * *